United States Patent

El-Rashidy

(10) Patent No.: US 9,408,865 B2
(45) Date of Patent: *Aug. 9, 2016

(54) TREATMENT OF HUNTINGTON'S DISEASE

(71) Applicant: Genix Therapeutics Group, LLC, Skokie, IL (US)

(72) Inventor: Ragab El-Rashidy, Deerfield, IL (US)

(73) Assignee: Genix Therapeutics Group, LLC, Skokie, IL (US)

( * ) Notice: Subject to any disclaimer, the term of this patent is extended or adjusted under 35 U.S.C. 154(b) by 24 days.

This patent is subject to a terminal disclaimer.

(21) Appl. No.: 14/539,305

(22) Filed: Nov. 12, 2014

(65) Prior Publication Data

US 2015/0071897 A1    Mar. 12, 2015

Related U.S. Application Data

(63) Continuation-in-part of application No. 13/838,631, filed on Mar. 15, 2013, now Pat. No. 8,889,125.

(51) Int. Cl.
*A61K 38/43* (2006.01)
*A61K 31/714* (2006.01)
*A61K 31/7076* (2006.01)
*A61K 31/675* (2006.01)
*A61K 31/455* (2006.01)
*A61K 9/00* (2006.01)
*A61K 9/19* (2006.01)
*A61K 31/51* (2006.01)

(52) U.S. Cl.
CPC .............. *A61K 31/714* (2013.01); *A61K 9/0019* (2013.01); *A61K 9/19* (2013.01); *A61K 31/455* (2013.01); *A61K 31/51* (2013.01); *A61K 31/675* (2013.01); *A61K 31/7076* (2013.01)

(58) Field of Classification Search
None
See application file for complete search history.

(56) References Cited

PUBLICATIONS

Sedico, Adeno-Sed B Forte drug information, 2004 (1 page).*

* cited by examiner

*Primary Examiner* — Kade Ariani
(74) *Attorney, Agent, or Firm* — Olson & Cepuritis, Ltd.

(57) ABSTRACT

The present invention relates to a method of treatment and/or ameliorating the symptoms of Huntington's disease comprising the step of administering an effective amount of adenosine triphosphate, co-carboxylase, nicotinamide, and cyanocobalamin in a physiologically acceptable carrier to an individual in need thereof. Preferably, the administration is via intramuscular injection.

5 Claims, No Drawings

TREATMENT OF HUNTINGTON'S DISEASE

CROSS-REFERENCE TO RELATED APPLICATION

This application is a continuation-in-part of U.S. application Ser. No. 13/838,631, filed on Mar. 15, 2013, now U.S. Pat. No. 8,889,125, the teachings of which are incorporated by reference herein in their entirety.

FIELD OF THE INVENTION

The present invention relates to treatment and/or amelioration of symptoms due to Huntington's disease and other related diseases due to polyglutamine accumulation and toxicity.

BACKGROUND OF THE INVENTION

Huntington's disease is an inherited, severely disabling, neurodegenerative disorder without curative or preventative treatment. It is caused by a genetic defect on chromosome 4. The defect causes a portion of the DNA, called a CAG repeat, to occur many more times than it is supposed to. Normally this section of DNA is repeated 10 to 28 times but in person's with Huntington's disease, it is repeated 36 to 120 times. As the gene is passed down through families the number of repeats tends to get larger. The larger the number of repeats, the greater the chance of developing symptoms at an earlier age.

Huntington's disease is a member of a group of diseases occurring due to polyglutamine accumulation and toxicity. It has a broad impact on a person's functional abilities and often results in movement, cognitive, and psychiatric disorders. Most people with Huntington's disease develop signs and symptoms in their mid-thirties to forties, but the onset could occur earlier or later in life. Symptoms include behavioral changes such as: hallucinations, irritability, moodiness, and restlessness; physical changes such as: facial movements, head turning to shift eye position, quick, sudden jerky movements of the arms, legs, or face, and slow uncontrolled movements; and cognitive changes such as: dementia, disorientation, loss of judgment, loss of memory, speech changes, and personality changes. Huntington's disease is ultimately fatal.

Several observations have led to the hypothesis that mitochondrial dysfunction has a role in polyglutamine diseases, and in Huntington's disease in particular. There is evidence which points to abnormal energy metabolism, elevated lactate levels, and impaired mitochondrial-complex activity. The implication of branched chain amino acids in mitochondrial intermediary metabolism, both in brain and peripheral tissues, further supports an important role for energy deficit in Huntington's disease. A reduction in adenosine triphosphate (ATP) production has been found in the brain of mice with Huntington's disease, including presymptomatic mice. In Huntington's disease patients, there is strong evidence for hypometabolism in the brain where glucose consumption is reduced, especially in the basal ganglia, even in presymptomatic mutation carriers. The underlying cause of this early energy deficit is not currently known, but impaired glycolysis, citric acid cycle, and/or oxidative phosphorylation may be involved.

The Unified Huntington's Disease Rating Scale (UHDRS) is an assess instrument used to evaluate the clinical features of Huntington's Disease. The UHDRS is a much-accepted measure for assessment of more global change in Huntington's disease and may be used in conjunction with a more specific measure, such as amelioration of hand grip strength, to assess improvement in Huntington's disease. An improvement in a measure such as hand grip strength may translate into improvements in quality of life or mood. The UHDRS was created to combine many important elements of various instruments and rating scales used to assess Huntington's Disease patients into a single comprehensive and reliable instrument. The UHDRS is used to assess four main domains of clinical performance and capacity: motor function, cognitive function, behavioral abnormalities, and functional capacity.

SUMMARY OF THE INVENTION

The present invention provides a method for treating or ameliorating the symptoms associated with neurodegenerative diseases such as Huntington's disease. The method comprises administration of a composition comprising adenosine triphosphate (ATP), co-carboxylase, nicotinamide, and cyanocobalamin in a pharmaceutically acceptable carrier. The present method provides improvement in the UHDRS in motor, cognitive, behavioral, and/or functional categories or a composite score composed of these categories.

ATP, co-carboxylase, nicotinamide, and cyancobalamin are coadminstered, preferably by intramuscular injection, to the patient in a respective weight ratio of 10-50 parts by weight ATP, 50-250 parts by weight co-carboxylase, 20-100 parts by weight nicotinamide, and 0.5-1 parts by weight cyanocobalamin, preferably in a respective weight ratio of about 20:100:40:1 in a physiologically acceptable liquid carrier such as water, physiological saline solution, and the like.

Another preferred method aspect consists essentially of ATP, co-carboxylase, nicotinamide, and cyanocobalamin being coadministered, preferably by intramuscular injection, to the patient in a respective weight ratio of about 50:250:100:1 in a physiologically acceptable liquid carrier such as water, physiological saline solution, and the like.

DETAILED DESCRIPTION OF PREFERRED EMBODIMENTS

ATP is a multifunctional nucleoside triphosphate used in cells as a coenzyme. ATP transports chemical energy within cells for metabolism. It is one of the end products of cellular respiration and used by enzymes and structural proteins in many cellular processes.

Co-carboxylase, also called thiamine pyrophosphate, is a thiamine (Vitamin B1) derivative present in all living systems, in which it catalyzes several biochemical reactions. Co-carboxylase works as a coenzyme in many enzymatic reactions, such as: pyruvate dehydrogenase complex, pyruvate decarboxylase complex in ethanol fermentation, alpha-ketoglutarate dehydrogenase complex, branched-chain amino acid dehydrogenase complex, 2-hydroxyphytanoyl-CoA lyase, and transketolase.

Nicotinamide is the amide of nicotinic acid (Vitamin B3/niacin). In cells, niacin is incorporated into nicotinamide adenine dinucleotide (NAD) and nicotinamide adenine dinucleotide phosphate (NADP). NAD+ and NADP+ are coenzymes in a wide variety of enzymatic oxidation-reduction reactions.

Cyanocobalamin is the most common and widely-produced of the chemical compounds that have vitamin activity as Vitamin B12. Cyanocobalamin is usually prescribed for the following reasons: after surgical removal of part or all of the stomach or intestine to ensure there are adequate levels of Vitamin B12 in the bloodstream; to treat pernicious anemia;

Vitamin B12 deficiency due to low intake from food; thyrotoxicosis; hemorrhage; malignancy; liver or kidney disease. Cyanocobalamin injections are often prescribed to gastric bypass patients having had part of their small intestine bypassed, making it difficult for B12 to be absorbed via food or vitamins. Vitamin B12 deficiency can cause severe and irreversible damage, especially to the brain and nervous system. Neurological symptoms include: sensory or motor deficiencies (absent reflexes, diminished vibration or soft touch sensation), subacute combined degeneration of spinal cord, or even symptoms of dementia and or other psychiatric symptoms such as irritability, focus/concentration problems and depressive state with suicidal tendencies.

The composition useful for practicing the present invention includes about 10 parts by weight adenosine triphosphate, about 50 parts by weight co-carboxylase, about 20 parts by weight nicotinamide, and about 0.5 parts by weight cyanocobalamin, in a pharmaceutically acceptable carrier as illustrated in Table 1, below.

TABLE 1

Therapeutic Composition

| Component | Preferred amount |
| --- | --- |
| adenosine triphosphate | 10 mg |
| co-carboxylase | 50 mg |
| nicotinamide | 20 mg |
| cyanocobalamin | 0.5 mg |

Inactive ingredients such as glycine, sodium hydroxide, thiomersal, and the like, can also be present.

A preferred dosage form is a lyophilized composition containing about 10 mg adenosine triphosphate, about 50 mg co-carboxylase, about 20 mg nicotinamide, and about 0.5 mg cyanocobalamin reconstituted in an aqueous 0.9% saline solution.

TABLE 2

Preferred Ranges of Components

| Component | Preferred range (mg) |
| --- | --- |
| adenosine triphosphate | 10-50 |
| co-carboxylase | 50-250 |
| nicotinamide | 20-100 |
| cyanocobalamin | 0.5-1 |

A preferred method for ameliorating Huntington's Disease symptoms, such as loss of grip strength in a patient suffering from Huntington's Disease, comprises administering to the patient an effective amount of a composition consisting essentially of ATP, co-carboxylase, nicotinamide, and cyanocobalamin in a physiologically acceptable carrier, wherein the administration is by intramuscular injection, and wherein the effective amount administered comprises about 10-50 mg adenosine triphosphate, about 50-250 mg co-carboxylase, about 20-100 mg nicotinamide, and about 0.5-1 mg cyanocobalamin as illustrated in Table 2, above.

Excess ATP is known to cause vasodilation, thus the upper limit of about 50 mg ATP should be monitored closely. An excessive dose of ATP may also elevate the level of uric acid in the patient's blood stream and trigger a case of gout.

Co-carboxylase (thiamine) administered in excess of about 250 mg/dose also may lower the patient's blood pressure and may give rise to allergic reactions.

Nicotinamide administered in excess of about 100 mg/dose may give rise to dizziness, headache, and nausea. Excessive doses of nicotinamide may also have a toxic effect on the liver.

Cyanocobalamin administered in excess of about 1 mg/dose also may give rise to allergic reactions, extreme thirst, and diarrhea.

A more preferred method for ameliorating Huntington's Disease symptoms, such as a loss of grip strength in a patient suffering from Huntington's Disease, comprises administering to the patient an effective amount of a composition consisting essentially of adenosine triphosphate, co-carboxylase, nicotinamide, and cyanocobalamin in a physiologically acceptable carrier, wherein the administration is by intramuscular injection, and wherein the effective amount administered comprises about 50 milligrams adenosine triphosphate, about 250 milligrams co-carboxylase, about 100 milligrams nicotinamide, and about 1.0 milligrams cyanocobalamin.

The method of the present invention can be practiced by administering the aforedescribed compositions intramuscularly. Preferably, the composition is administered intramuscularly three (3) times per week, i.e. every other day.

EXAMPLE

A 66 year-old male patient presenting symptoms of Huntington's disease was treated by intramuscular injection of the therapeutic composition shown in Table 1, above. The therapeutic composition was administered intramuscularly every other day over a period of one month. After the one-month treatment, accompanied by physical therapy, the patient reported improvement in daily functioning, an improved average grip strength in the left hand (from 57 pounds to 66 pounds) while maintaining the same average grip strength (59 pounds) in the right hand.

Intramuscular administration of the therapeutic composition shown in Table 1 was continued for 57 months with the same dosage and frequency of administration.

Upon examination, the patient exhibited an average grip strength in the left hand of 52.3 pounds and an average grip strength in the right hand of 44 pounds.

Over the aforesaid 57-month period the time during the 9-hole peg test for the left hand had only increased from 32 seconds to 42.28 seconds.

Comparison of current MRI brain scan with a MRI brain scan made before initiation of the aforedescribed treatment indicated no parenchymal abnormalities, no new masses, intercranial hemorrhage, or extra-axial fluid collections. No evidence of restricted diffusion to suggest acute ischemia or infarction was noted.

The foregoing description is intended as illustrative and is not to be taken as limiting. Still other variants within the spirit and scope of the present invention are possible and will readily present themselves to those skilled in the art.

The invention claimed is:

1. A method for ameliorating loss of grip strength in a patient suffering from Huntington's Disease which comprises administering to the patient an effective amount of a composition comprising adenosine triphosphate, co-carboxylase, nicotinamide, and cyanocobalamin in a physiologically acceptable carrier, wherein the administration is by intramuscular injection, and wherein the effective amount administered comprises about 10-50 parts by weight adenosine triphosphate, about 50-250 parts by weight co-carboxylase, about 20-100 parts by weight nicotinamide, and about 0.5-1 parts by weight cyanocobalamin.

2. The method in accordance with claim 1 wherein the intramuscular injection is effected on alternate days.

3. The method in accordance with claim 2 wherein the effective amount administered comprises about 50 milligrams adenosine triphosphate, about 250 milligrams co-carboxylase, about 100 milligrams nicotinamide, and about 1 milligram cyancobalamin.

4. A method for ameliorating loss of grip strength in a patient suffering from Huntington's Disease which comprises administering to the patient an effective amount of a composition comprising adenosine triphosphate, co-carboxylase, nicotinamide, and cyanocobalamin in a physiologically acceptable carrier, wherein the administration is by intramuscular injection, and wherein the effective amount administered comprises about 10-50 parts by weight adenosine triphosphate, about 50-250 parts by weight co-carboxylase, about 20-100 parts by weight nicotinamide, and about 0.5 parts by weight cyanocobalamin.

5. A method for ameliorating loss of grip strength in a patient suffering from Huntington's Disease which comprises administering to the patient an effective amount of a composition comprising adenosine triphosphate, co-carboxylase, nicotinamide, and cyanocobalamin in a physiologically acceptable carrier, wherein the administration is by intramuscular injection, and wherein the effective amount administered comprises about 50 milligrams adenosine triphosphate, about 250 milligrams co-carboxylase, about 100 milligrams nicotinamide, and about 1 milligram cyanocobalamin.

\* \* \* \* \*